United States Patent [19]

Vité et al.

[11] 4,299,818
[45] Nov. 10, 1981

[54] CONTROL OF INSECTS WITH 3,3,7-TRIMETHYL-2,9-DIOXATRICYCLO[3.3.1.0$^{4,7}$]NONANE IN MIXTURE WITH ETHANOL, AND OPTIONALLY, α-PINENE

[75] Inventors: Jean P. Vité, Freiburg, Fed. Rep. of Germany; Alf Bakke, Ås, Norway

[73] Assignee: Borregaard Industries Limited, Norge, Sarpsborg, Norway

[21] Appl. No.: 171,841

[22] Filed: Jul. 24, 1980

[30] Foreign Application Priority Data

Jul. 25, 1979 [NO] Norway ................................ 792454

[51] Int. Cl.$^2$ ........................................... A01N 25/00
[52] U.S. Cl. ..................................................... 424/84
[58] Field of Search .......................................... 424/84

[56] References Cited

PUBLICATIONS

Castek et al., J. of Econ. Entomology, vol. 60, No. 3, pp. 658–660, Jun. 1967.
Jacobson, "Insect Sex Pheromones", (1972) published by Academic Press, pp. 78, 275, 204 & 205.
Bauer et al., (J. P. Vite), Naturwissenschaften 62 (1975), p. 539.
Chem. Abstracts, vol. 88: 101805p (1978).
Vité et al., Naturwissenschaften, vol. 66 (1979), pp. 528–529.

Primary Examiner—Donald B. Moyer
Attorney, Agent, or Firm—Wenderoth, Lind & Ponack

[57] ABSTRACT

A combination of lineatin, ethanol and optionally other naturally occurring components in trees which are normally attacked by Ambrosia beetles, and the use thereof as an attractant for combatting Ambrosia beetles (Trypodendron), particularly *T. lineatum*.

10 Claims, No Drawings

CONTROL OF INSECTS WITH 3,3,7-TRIMETHYL-2,9-DIOXATRICYCLO[3.3.1.0⁴,⁷]NONANE IN MIXTURE WITH ETHANOL, AND OPTIONALLY, α-PINENE

This invention relates to a composition for combatting certain species of Ambrosia beetles (Trypodendron), pests which do serious harm in the forest. The two particularly important species are *T. lineatum* which attacks conifers, and *T. domesticum* which attacks hardwood.

One way of controlling Ambrosia beetles and other bark beetles is the use of pesticides, but these have limited use, mainly for two reasons. Firstly, it is difficult to obtain a good effect since the beetles live hidden under the bark most of the time, and secondly, it is desired as far as possible to avoid the use of chemicals which may disturb the forest ecological system.

In the fight against bark beetles a search has therefore been made during the last years for new methods. It has been found that it may be suitable to disturb the communication system of the bark beetles, which primarily is of chemical nature. Under certain conditions the beetles produce communication substances, inter alia, from resin in the attacked trees. The substances are emitted to the surroundings and affect other individuals of the same species. Such substances, which have been named pheromones, are widespread in nature and can be perceived even in very small amounts by these insects. When the communication substance has been picked up, it stimulates certain reactions in the recipient. Some communication substances will have an attractive effect, while others will, for instance, have an exciting or alarming effect.

It is known that the pheromone, 3,3,7-trimethyl-2,9 dioxatricyclo[3.3.1.0⁴,⁷]nonane, called lineatin, is an important component of the signal system of the Ambrosia beetles.

It is known that Ambrosia beetles select individual tree trunks or logs while other logs in the same pile are not attacked. We assumed that this was caused by the fact that lineatin, which undoubtedly has an attractive effect on Ambrosia beetles, is not the only factor which is responsible for the individual trunk or log being attacked. To test this theory we mounted perforated cylinder traps simulating tree trunks, with synthetic lineatin inside. Flight traps with lineatin as the only attractant (traps in which the beetles are caught during the flight even when they do not attack the logs) were also mounted. During these tests it was found that only a small catch of beetles was made with the perforated cylinder traps, while a considerable catch was made with the flight traps. This confirms that lineatin induces aggregation in the area, but is not sufficient to cause the beetles to attack the logs (the perforated cylinder traps). Since perforated cylinder traps of different types have been found to be considerably more suitable under other circumstances than flight traps, it would therefore be preferable to use perforated cylinder traps for combatting Ambrosia beetles.

It is known that ethanol has a small, but nevertheless detectable, attractive effect on Ambrosia beetles and that α-pinene increases this effect on *T. lineatum*, but reduces it drastically on *T. domesticum*.

Surprisingly, we have found that an attractant consisting of lineatin and ethanol and, optionally, other natural components of the tree normally attacked by the Ambrosia beetle, placed in a perforated cylinder trap, attracts many times the amount of beetles caught when lineatin alone is used as attractant. An explanation of this is that the lineatin attracts the beetles to the area in question, while ethanol and other natural components provoke the attack by the beetles. With respect to the perforated cylinder traps this attack will consist of the beetles crawling through the perforations in the trap, where they are then caught.

The naturally occurring substances which may be used in the attractant for *T. lineatum* may be terpenes such as α-pinene, β-pinene and myrcene. By means of an attractant consisting of lineatin and ethanol and, optionally, other naturally occurring components as mentioned above, considerable amounts of the detrimental beetles are caught in suitable traps. The tests made are described more extensively in the following.

Three types of traps were used. One type was a flight trap consisting of a polyethylene window 60×55 cm attached to strings tied between trees above an aluminium funnel having a diameter of 60 cm and equipped with a collecting jar, called in the following a "window trap". The second trap was a cone-shaped, perforated cylinder, 100 cm high, 20 cm in diameter at the top and 35 cm at the bottom. The trap was provided with perforations having a diameter of 2.5 mm, and had a slightly rough surface, while the inside was smooth to prevent the trapped insects from escaping. This type of trap is called in the following a "cone trap". The third type of trap was a cylindrical pipe, 120 cm high, diameter 12 cm, provided with a collecting jar at the bottom and perforations as in the cone traps. This type of trap has been called a "pipe trap".

Ethanol alone or in a mixture of 4 parts to 1 part of α-pinene was released from glass vials 50 mm in length and 9 mm in diameter covered with a perforated plastic stopper. Neat lineatin diluted in n-pentane in the ratio 1100 was released from a glass capillary (40 mm in length, 0.9 mm in diameter) closed at the bottom. A total of 1.5 to 2.0 mg of diluted lineatin per trap resulted in reasonable catches over a period of several days. The vials and the capillaries containing said substances were attached to the window traps and to the inside bottom of the cone traps and the pipe traps. The traps were arranged in a square pattern. For some of the test no empty control traps were used, as previous tests have shown that only accidental catches of single beetles occur with window traps.

The results attained are illustrated in the following tables:

TABLE 1

Catch of *T. domesticum* by window traps with lineatin as bait in two tests.

| Bait | Average number (and extremes) of beetles caught per trap | | Sex ratio ♂:♀ |
|---|---|---|---|
| Lineatin + ethanol | 156 | (141–171) | 1:0.84 |
| Lineatin + α-pinene | 45.5 | (42–50) | 1:0.46 |
| Lineatin + ethanol + α-pinene | 37.5 | (23–52) | 1:1.27 |

TABLE 2

Catch of T. lineatum by flight traps (window traps) and perforated cylinders (cone) with lineatin ("lin.") as bait.

| Period | Type of traps | Bait | Repetitions | Average number (and extremes) of beetles caught per trap | | Sex ratio ♂:♀ | % of total catch |
|---|---|---|---|---|---|---|---|
| May 18-21 | window | Lin. + ethanol | 9 | 140 | (50-232) | 1:0.96 | 34.8 |
| | cone | Lin. + ethanol + α-pinene | 3 | 244.7 | (219-295) | 1:0.67 | 60.7 |
| | cone | Lin. | 3 | 18.3 | (11-26) | 1:0.17 | 4.5 |
| May, 21-22 | window | Lin. + ethanol + α-pinene | 3 | 78 | (52-95) | 1:0.76 | 41.2 |
| | cone | Lin. + ethanol + α-pinene | 3 | 65.7 | (43-109) | 1:0.70 | 34.7 |
| | window | Lin. | 3 | 43 | (31-50) | 1:0.57 | 22.7 |
| | cone | " | 3 | 2.7 | (0-5) | — | 1.4 |
| May 22-25 | window | Lin. + ethanol + α-pinene | 3 | 62.3 | (52-68) | | 18.4 |
| | cone | Lin. + ethanol + α-pinene | 3 | 164.7 | (87-266) | | 48.9 |
| | window | Lin. + ethanol | 3 | 59 | (38-86) | | 17.5 |
| | cone | " | 3 | 52 | (43-58) | | 15.4 |

TABLE 3

Catch of T. lineatum in perforated cylinder traps with lineatin as bait.

| Type of trap | Bait | Average number (and extremes) of beetles caught per trap | | Sex ratio ♂:♀ | % of total catch |
|---|---|---|---|---|---|
| Cone+ | Lineatin + ethanol + α-pinene | 244.7 | (219-295) | 1:0.7 | 93 |
| | Lineatin | 18.3 | (11-26) | 1:02 | 7 |
| Pipe++ | Lineatin + ethanol + α-pinene | 184.3 | (103-288) | | 91 |
| | Lineatin | 17.3 | (12-24) | | 9 |
| | Ethanol + α-pinene | 0.3 | (9-1) | | — |
| | Control | 0 | | | — |

+ = "Konusfalle" (Rochling, Haren/Ems, Germany) 20/35 × 100 cm
++ = "kamrør" trap (Borregaard, Sarpsborg, Norway) 12 × 120 cm As will be seen from the tables a good catch of T. lineatum is obtained with a bait comprising lineatin and ethanol, and the best results are attained when the composition also comprises a third component, such as α-pinene. The improved effect is particularly marked when the composition is used in perforated cylinder traps of the cone and pipe type.

The amount of the active components, lineatin and ethanol and, optionally, a third component, such as α-pinene, in the composition is ideally such that the composition during the whole time of its use emits all said active components, i.e. so that the active components are used up at approximately the same time. Such an adjusted evaporation can be obtained both by varying the amount of the active components in the composition and also by varying the design of the composition. The composition may for instance consist of a multi-layer impregnated material, or the active components may be cast in a solid, volatile solvent, such as wax. Further, the composition may be as used in the tests described above, wherein the components are contained separately or in admixture in vials or capillaries, or, preferably in tape form.

We claim:

1. A composition for attracting Ambrosia beetles of the genus Trypodendron, comprising lineatin and ethanol in a combined amount which is effective to attract the beetles.

2. A composition according to claim 1, wherein the relative amounts of the lineatin and ethanol in the composition are such that, under the conditions in which the composition is used to attract the beetles, the lineatin and ethanol will both become fully depleted at approximately the same time.

3. A composition according to claim 1, further comprising a terpene selected from the group consisting of α-pinene, β-pinene and myrcene, the combined amount of the lineatin, ethanol and terpene being effective to attract the beetles.

4. A composition according to claim 3, wherein the relative amounts of the lineatin, ethanol and terpene in the composition are such that, under the conditions in which the composition is used to attract the beetles, the lineatin, ethanol and terpene will all become fully depleted at approximately the same time.

5. A composition according to claim 3 or 4, wherein the terpene is α-pinene.

6. A method of attracting Ambrosia beetles of the genus Trypodendron, which comprises exposing the beetles to a composition comprising lineatin and ethanol in a combined amount which is effective to attract the beetles.

7. A method according to claim 6, wherein the relative amounts of the lineatin and ethanol in the composition are such that, under the conditions in which the composition is used to attract the beetles, the lineatin and ethanol will both become fully depleted at approximately the same time.

8. A method according to claim 6, wherein the composition further comprises a terpene selected from the group consisting of α-pinene, β-pinene and myrcene, the combined amount of the lineatin, ethanol and terpene being effective to attract the beetles.

9. A method according to claim 8, wherein the relative amounts of the lineatin, ethanol and terpene in the composition are such that, under the conditions in which the composition is used to attract the beetles, the lineatin, ethanol and terpene will all become fully depleted at approximately the same time.

10. A method according to claim 8 or 9, wherein the terpene is α-pinene.

* * * * *